US006589232B1

United States Patent
Mueller

(10) Patent No.: US 6,589,232 B1
(45) Date of Patent: Jul. 8, 2003

(54) SELECTIVE TREATMENT OF ENDOCARDIAL/MYOCARDIAL BOUNDARY

(76) Inventor: Richard L. Mueller, 2305 Cypress Point, Byron, CA (US) 94514

(*) Notice: Subject to any disclaimer, the term of this patent is extended or adjusted under 35 U.S.C. 154(b) by 0 days.

(21) Appl. No.: 09/550,932

(22) Filed: Apr. 17, 2000

Related U.S. Application Data

(62) Division of application No. 08/978,036, filed on Nov. 25, 1997, now Pat. No. 6,156,029.

(51) Int. Cl.$^7$ .............................................. A61B 18/18

(52) U.S. Cl. ........................ 606/15; 606/185; 604/95.05

(58) Field of Search ............................... 606/1, 2, 7, 8, 606/13–17, 32, 41, 45, 49, 185, 213; 607/89; 604/95.01, 95.05

(56) References Cited

U.S. PATENT DOCUMENTS

| | | | |
|---|---|---|---|
| 4,658,817 A | * | 4/1987 | Hardy |
| 4,784,133 A | | 11/1988 | Mackin |
| 4,790,310 A | | 12/1988 | Ginsburg et al. |
| 4,846,171 A | | 7/1989 | Kauphusman et al. |
| 4,913,142 A | * | 4/1990 | Kittrell et al. |
| 5,026,366 A | | 6/1991 | Leckrone |
| 5,188,634 A | | 2/1993 | Hussein et al. |
| 5,217,454 A | | 6/1993 | Khoury |
| 5,304,167 A | | 4/1994 | Freiberg |
| 5,370,675 A | * | 12/1994 | Edwards et al. |
| 5,389,096 A | | 2/1995 | Aita et al. |
| 5,454,782 A | | 10/1995 | Perkins |
| 5,464,394 A | | 11/1995 | Miller et al. |
| 5,464,404 A | | 11/1995 | Abela et al. |
| 5,466,234 A | | 11/1995 | Loeb et al. |
| 5,484,433 A | | 1/1996 | Taylor et al. |
| 5,591,159 A | | 1/1997 | Taheri |

(List continued on next page.)

FOREIGN PATENT DOCUMENTS

| | | |
|---|---|---|
| EP | 0 797 957 A1 | 10/1997 |
| WO | WO 96/35469 | 11/1996 |
| WO | WO 97/18768 | 5/1997 |
| WO | WO 97/25101 | 7/1997 |
| WO | WO 98/19614 | 5/1998 |
| WO | WO 99/08612 | 2/1999 |
| WO | WO 99/22658 | 5/1999 |

OTHER PUBLICATIONS

Kohmoto, Takushi, MD et al., "Assessment of Transmyocardial Perfusion in Alligator Hearts," Departments of Surgery, Medicine and Pathology, Columbia University, New York, NY, and the Department of Zoology, University of Florida, Gainesville. Nov. 14, 1996, pp. 1585–1591.

*Primary Examiner*—Roy D. Gibson
(74) *Attorney, Agent, or Firm*—Gibson, Dunn & Crutcher LLP

(57) ABSTRACT

A method for treating myocardium using at least one mechanical or electromagnetic energy functional device for forming a network of branched, interconnecting passages in a boundary between endocardium and myocardium, thereby enhancing blood flow into the treated zone, and a device for selectively treating ischemic myocardium tissue comprising a tube having proximal end and distal end, and at least one hollow lumen and defining an axis, at least two mechanical or electromagnetic energy functional devices disposed within the tube, the at least two mechanical or electromagnetic energy functional devices each having a distal end disposed adjacent the distal end of the central tube, and a deflecting member adjacent the distal portion of the central tube for deflecting the distal end of each of the at least two mechanical or electromagnetic energy functional devices away from the axis, for enabling treatment of selective areas of ischemic or hibernating myocardium tissue.

10 Claims, 14 Drawing Sheets

U.S. PATENT DOCUMENTS

| | | | |
|---|---|---|---|
| 5,607,421 A | | 3/1997 | Jeevanandam et al. |
| 5,642,736 A | * | 7/1997 | Avitall |
| 5,643,253 A | * | 7/1997 | Baxter et al. |
| 5,662,124 A | | 9/1997 | Wilk |
| 5,683,366 A | | 11/1997 | Eggers et al. |
| 5,725,521 A | | 3/1998 | Mueller .................... 606/7 |
| 5,725,523 A | | 3/1998 | Mueller .................... 606/15 |
| 5,730,741 A | | 3/1998 | Horzewski et al. ........... 606/1 |
| 5,755,714 A | * | 5/1998 | Murphy-Chutorian |
| 5,766,163 A | | 6/1998 | Mueller et al. ............ 606/7 |
| 5,766,164 A | | 6/1998 | Mueller et al. ............ 606/15 |
| 5,785,702 A | | 7/1998 | Murphy-Chutorian et al. . 606/7 |
| 5,855,577 A | | 1/1999 | Murphy-Chutorian et al. . 606/7 |
| 5,857,997 A | * | 1/1999 | Cimino et al. |
| 5,873,865 A | | 2/1999 | Horzewski et al. ......... 604/280 |
| 5,876,373 A | * | 3/1999 | Giba et al. .................... 604/95 |
| 5,893,848 A | * | 4/1999 | Negus et al. |
| 5,913,853 A | * | 6/1999 | Loeb et al. ................. 606/15 |
| 5,931,834 A | * | 8/1999 | Murphy-Chutorian et al. . 606/7 |
| 6,030,380 A | * | 2/2000 | Auth et al. .................. 606/41 |
| 6,066,131 A | * | 5/2000 | Mueller et al. .............. 606/15 |
| 6,106,520 A | * | 8/2000 | Laufer et al. ............... 606/32 |

* cited by examiner

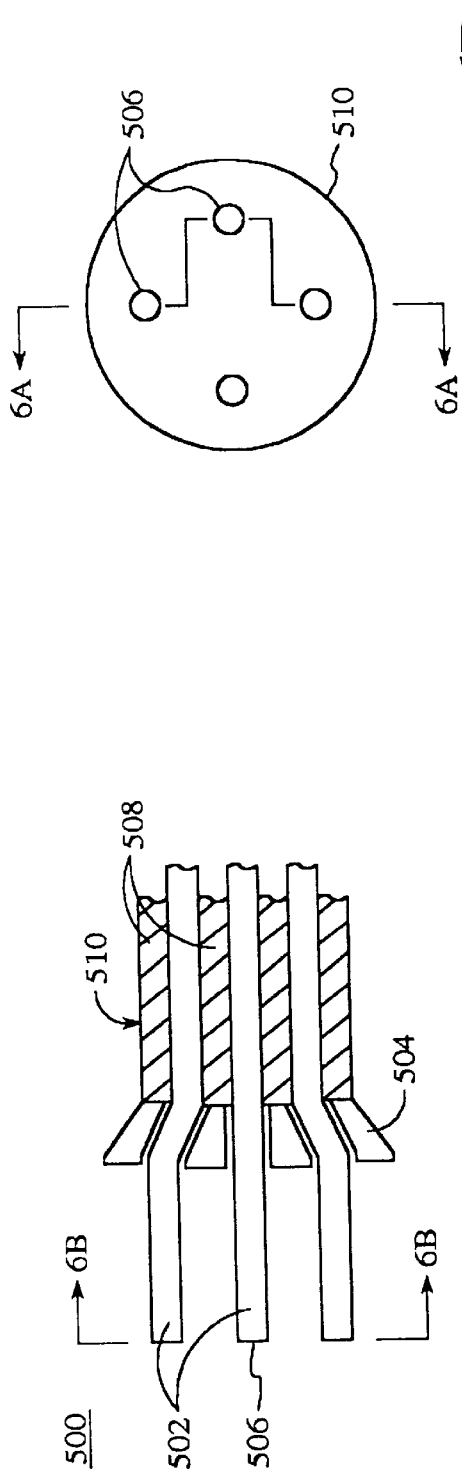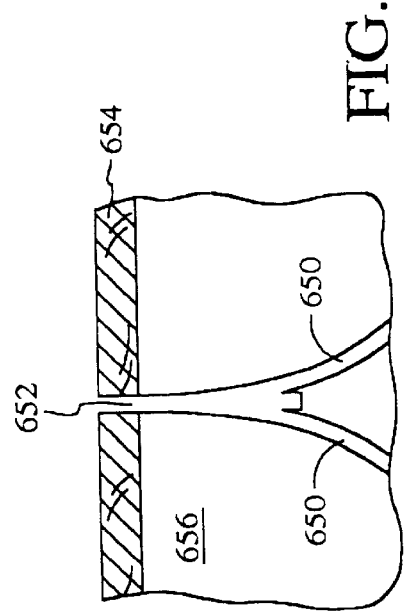
FIG. 6B
FIG. 7B
FIG. 6A

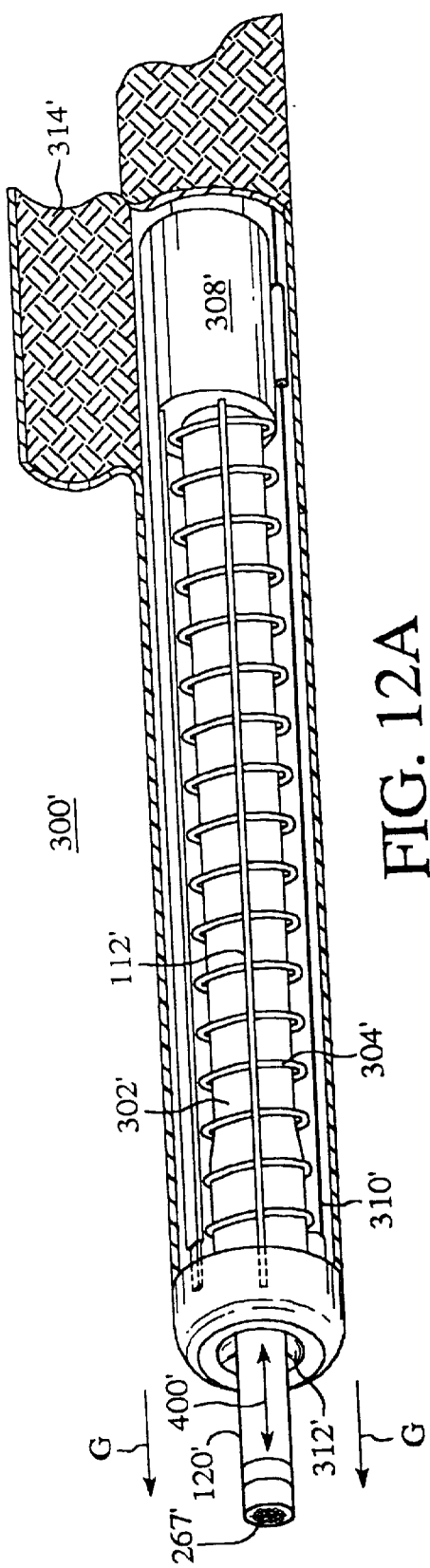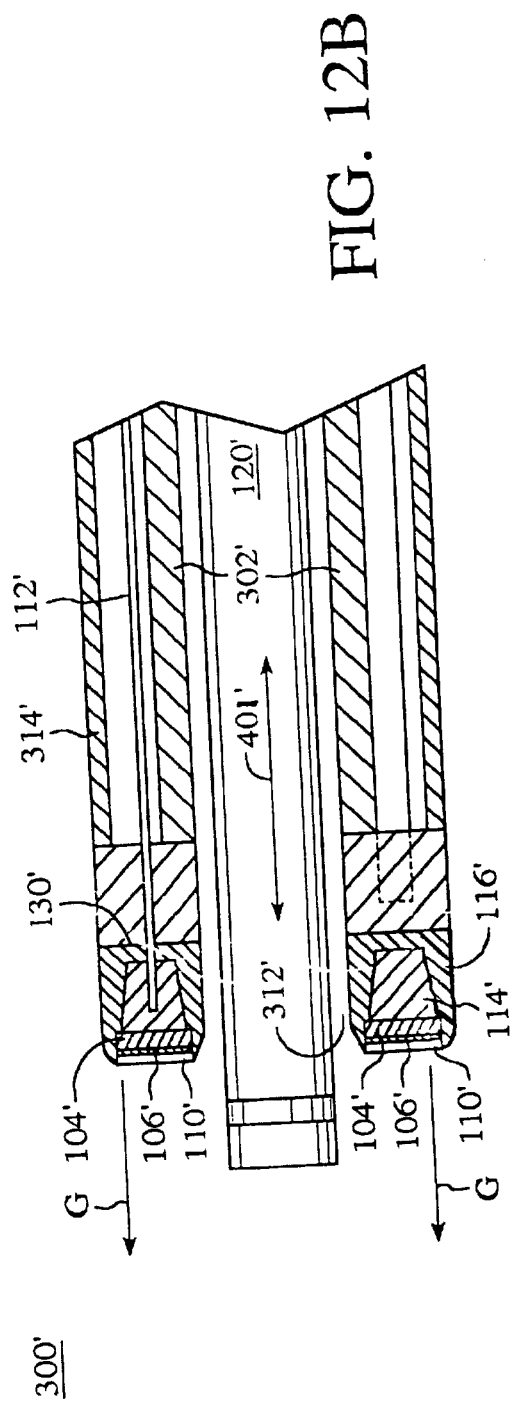
FIG. 12A
FIG. 12B

SELECTIVE TREATMENT OF ENDOCARDIAL/MYOCARDIAL BOUNDARY

RELATED APPLICATIONS

This application is a divisional of U.S. patent application Ser. No. 08/978,036, entitled "SELECTIVE TREATMENT OF ENDOCARDIAL/MYOCARDIAL BOUNDARY," filed Nov. 25, 1997 now U.S. Pat. No. 6,156,029.

FIELD OF THE INVENTION

The present invention relates generally to interventional devices for medical procedures. More particularly, the invention relates to selective treatment of ischemic or infarcted myocardium, with mechanical and electromagnetic energy functional devices, for simulating extension of the boundary between myocardial and endocardial layers within the heart. The invention is particularly adapted for simulating extension of the endocardial layer into the myocardium and for treating hibernating tissue zones.

BACKGROUND OF THE INVENTION
Transmyocardial Revascularization

In the treatment of heart disease, one method of improving myocardial blood supply is called transmyocardial revascularization (TMR), the creation of channels in the myocardium of the heart. The procedure using needles in a form of surgical "myocardial acupuncture" has been used clinically since the 1960s. Deckelbaum. L. I., Cardiovascular Applications of Laser Technology, *Lasers in Surgery and Medicine* 15:315–341 (1994). The technique relieves ischemia by causing angiogenesis and allowing blood to pass from the ventricle through the channels either directly into other vessels communicating with the channels or into myocardial sinusoids which connect to the myocardial microcirculation.

In the reptilian heart, perfusion of the myocardium occurs via communicating channels between the left ventricle and the coronary arteries. Frazier, O. H., Myocardial Revascularization with Laser—Preliminary Findings, *Circulation*, 1995; 92 [suppl II]:II-58-II-65. There is evidence of these communicating channels in the developing human embryo. In the human heart, myocardial microanatomy involves the presence of myocardial sinusoids. These sinusoidal communications vary in size and structure, but represent a network of direct arterial-luminal, arterial-arterial, arterial-venous, and venous-luminal connections. This vascular mesh forms an important source of myocardial blood supply in reptiles but its role in humans is poorly understood.

This is confirmed by recent research and a recent article. A greater proportion of reptilian endocardium and myocardium is supplied with oxygenated blood from the left ventricle itself, as opposed to the coronary arteries. Reptilian endocardium is relatively thicker and more-sponge-like than human myocardium, deriving from the extensive network of sinusoids and large channels emanating from the left ventricle and richly innervating the myocardium, thereby providing an increased effective surface area for blood flow, also known as "washing", and transfer of oxygen and nutrients to the myocardium. In the research protocol, after explanation and instrumentation, alligator hearts were perfused via the coronary arteries as well as via "washing" from the left ventricle. Using microspheres to estimate myocardial perfusion in the beating hearts, it was shown that although the epicardium was well perfused by the coronary arteries, a significant proportion of endocardial perfusion was from the ventricular chamber rather than the coronary arteries. Kohmoto, T. et al, *Assessment of Transmyocardial Perfusion in Alligator Hearts,* Circulation, Vol. 95, No. 6, Mar. 18, 1997.

Apparatus and methods for extending the thickness of endocardial tissue, and increasing oxygen and nutrient transport by washing of blood through the left ventricle, are virtually unknown. Conventionally, a process called transmyocardial revascularization is directed to forming a discrete number of spaced-apart channels, surgically from an epicardial surface through epicardium (TMR) or percutaneously through the left ventricle directly into myocardial tissue (PTMR). However, conventional TMR/PTMR does not create a dense pattern of stimulus injuries placed to simulate extension of the porous endocardium. TMR also does not focus treatment on the endocardial/myocardial boundary regions where ventricular washing flow via endocardium can enhance angiogenesis. Furthermore, treating hidden zones of hibernating, infarct-damaged or other types of tissue with a denser pattern of stimulation pathways is desirable and may be accomplished using the apparatus and methods for selective treatment of the endocardial/myocardial boundary.

ADVANTAGES AND SUMMARY OF THE INVENTION

Thus, it is an advantage of the present invention to provide an apparatus and method of use for selective myocardial revascularization, which overcomes the limitations of the prior art.

It is another advantage of the present invention to provide an apparatus and method especially adapted for selective treatment of hibernating tissue, infarct-damaged or other types of tissue best treated selectively.

It is a further advantage of the present invention to provide an apparatus with one or more fiber optic laser delivery means for effecting selective treatment of the endocardial/myocardial boundary.

It is a further advantage of the present invention to provide a catheter apparatus for placement within a heart chamber, organ aperture or other body opening, the apparatus having at least one lumen for guiding an energy delivery device or mechanical device to selected surfaces of the heart, heart chamber, organ aperture or other body opening for treatment thereon, particularly adapted for selective treatment of the endocardial/myocardial boundary.

Yet an additional advantage and object of the present invention is to provide a multiple channel type surgical or minimally invasive surgical apparatus for percutaneous, surgical or minimally invasive surgical use for creation of a plurality of stimulation zones or myocardial channels co-extending from a single epicardial, myocardial or endocardial point or position.

Another advantage and object of the present invention is to provide a surgical apparatus for performing selective treatment from an epicardial surface.

It is a further advantage of the present invention to provide an optimized amount of trauma or means of injury specific to or within a boundary, such as between endocardium and myocardium, or between infarct and non-infarct boundaries, naturally provided with ventricular blood via the highly vascularized endocardium.

Another advantage of the present invention is to treat boundary regions by minimizing or otherwise preventing undesirable and unnecessary lasing or other mechanical damage to existing endocardium, or epicardium, to gain access to the boundary region by piercing through the endocardium or epicardium to a depth which allows creation of the injury only at the selected boundary region.

In summary, the present invention is an apparatus for placement within a heart chamber, organ aperture, chest cavity or other body opening. The apparatus has at least one lumen for guiding an energy delivery device or mechanical device to selected surfaces of a heart or heart chamber for treatment thereon. The distal tip of the device has one or more functional devices extending therefrom, optionally having a deflection control mechanism therein. The apparatus can be used in conjunction with a fiber optic or other laser delivery means, mechanical intervention means, radio frequency device, microwave device, ultrasound device or fluid jets.

In a preferred embodiment, the invention comprises a transluminal catheter having a proximal end and a distal end and at least one lumen with a handle portion at the proximal end and a treatment device deflecting mechanism, such as a ball or cone, at the distal end. One or more, preferably several, treatment devices can be advanced out the distal end of the lumen, and deflected by the ball or cone at an angle to provide a relatively dense multiple pattern of treatment points from adjacent a single site. By forming a large number of mechanical or energy incisions through the endocardium and in myocardium, i.e. in the endocardial/myocardial boundary, the treated myocardial area will have endocardium-like properties, including providing a greater surface area and higher efficiency of oxygen and nutrient transfer via blood washing of the untreated myocardium through the intact and densely profused endocardium which receives a large amount of oxygenated blood via the ventricle.

In a preferred embodiment, the invention is a surgical and minimally invasive surgical handpiece with advancement mechanism to allow insertion of an energy or mechanical device through the epicardial surface to a desired depth where deployment of multiple treatment devices can occur to create a relatively dense pattern of injury in several millimeters of myocardium adjacent a border with endocardium and into the endocardium.

A novel method of locating and treating zones of myocardial tissue, such as adjacent a boundary, which have been damaged by infarct or otherwise is also disclosed using described apparatus. Such hidden or hibernating zones are treatable by extending individual optical fibers or fiber bundles therein, so as to effectively create a dense pattern of injury from the ventricle through healthy endocardial tissue, or from the epicardium, into the hibernating zones. The method treats boundary regions by minimizing or otherwise preventing undesirable and unnecessary lasing or other mechanical damage to existing endocardium to gain access to the boundary region. Piercing tools are described to facilitate advancement to the selected boundary prior to creation of the injury.

Numerous other advantages and features of the present invention will become readily apparent from the following detailed description of the invention and the embodiments thereof, from the claims and from the accompanying drawings.

BRIEF DESCRIPTION OF THE DRAWINGS

FIGS. 6A and 6B are representative cross sectional and section views, respectively, of another preferred embodiment of a selective treatment of the endocardial/myocardial boundary system 500 of the present invention.

FIG. 7B is representative view of a branched, contiguous, multi-channeled, sinusoidal and interconnected treatment zone.

FIGS. 12A, 12B and 12C are representative isometric and section views of the distal end and steering system of a preferred embodiment of a catheter ultrasound guidance system 300' for forming sinusoidal and interconnected channels or treatment zones in endocardial/myocardial boundary.

DETAILED DESCRIPTION OF THE PREFERRED EMBODIMENT

Figure 1:
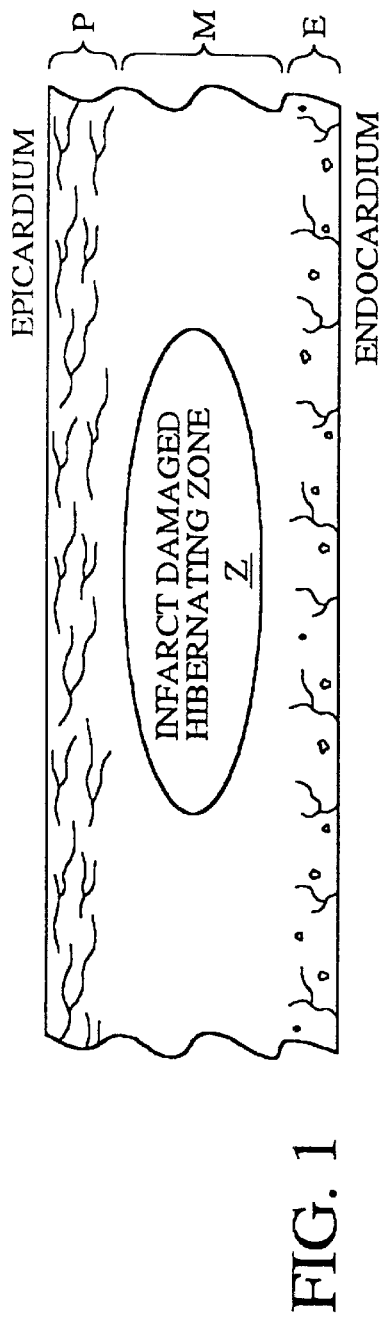
FIG. 1 is a representative section view of cardiac tissue, including endocardium, epicardium, myocardium and a typically central, hibernating, infarct damaged zone of myocardial tissue.

It will be understood that while numerous preferred embodiments of the present invention are presented herein, many of the individual elements and functional aspects of the embodiments are similar. Therefore, it will be understood that structural elements of the numerous apparatus disclosed herein having similar or identical function will have like reference numerals associated therewith. All of the devices disclosed and described herein are suitable for selective treatment of ischemic tissue. The devices may be used to treat myocardium bordering endocardium so that the treated area simulates endocardium physically and in function, thereby resulting in "endocardial extension". The same devices may be used to selectively treat other areas of heart tissue, particularly hibernating myocardium.

FIG. 1 is a representative section view of cardiac tissue, including endocardium E, epicardium P and a typically central, hibernating, infarct damaged zone of tissue Z surrounded by conventional myocardium M. Zones of tissue Z which are oxygen or nutrient starved are generally denser and can be located via an angiogram or felt by the gloved finger of a physician performing an exploration. Such damaged zones may be the result of an infarction, damaging arrhythmia, other physical, chemical or electrical assault or event, etc. In TMR type treatments, these hibernating zones can be treated by mechanically piercing or channeling using sharpened needles and blades, mechanical drills and/or energy delivery devices, such a lasers, radio frequency devices, microwave energy, ultrasound energy, and fluid jets.

The treatment differs from conventional TMR or PTMR in several important ways. For example, as compared to TMR or PIMP, fewer or no trans-myocardial channels are created. In "endocardial extension" or selective treatment of the endocardial/myocardial boundary, the endocardial/myocardial boundary is treated using a denser pattern of small laser or mechanical or otherwise created injury sites, i.e. sites for angiogenesis and/or stimulation zones, adjacent to the healthy endocardium. These injuries are specifically located adjacent one of the best natural, localized sources of oxygenated blood, i.e. the left ventricle and endocardium. Treatment also is designed to selectively treat myocardium by simulating conversion of the inner-most several millimeters of myocardium into tissue similar to adjacent endocardium, having decreased density resulting from a relatively dense stimulation zone or injury pattern. It will be understood that although the apparatus and methods of the present invention are described with a great deal of particularity, selective treatment of the endocardial/myocardial boundary treatment may be done generally from either endocardial or epicardial surfaces, both of which procedures are included within the scope of the present invention. Also, selective treatment of hibernating tissue is performed using same or similar dense treatment patterns of pathways, interconnected physically and through effects and results of angiogenesis.

Figure 2A:
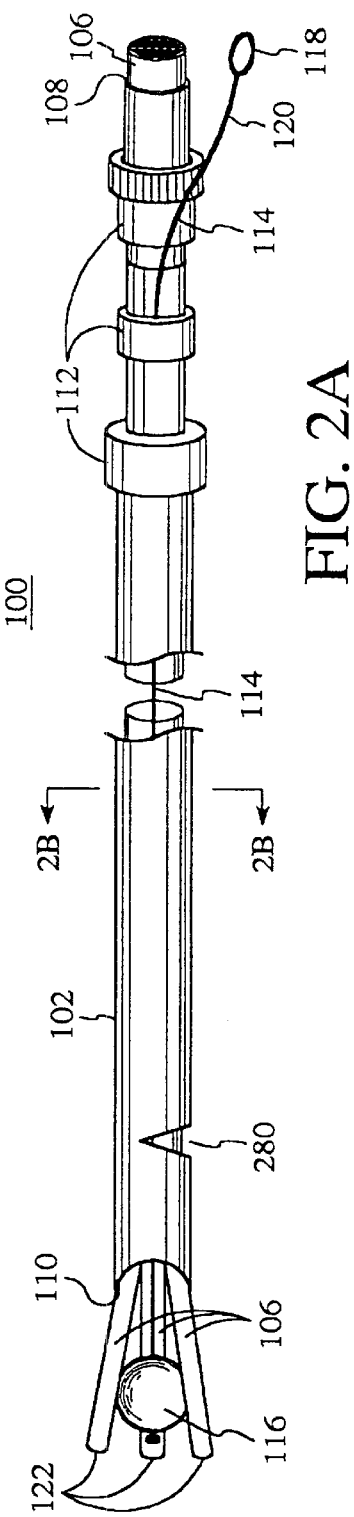
FIG. 2A is a representative perspective view of a preferred embodiment of a selective treatment of the endocardial/myocardial boundary system 100 of the present invention.
Figure 2B:
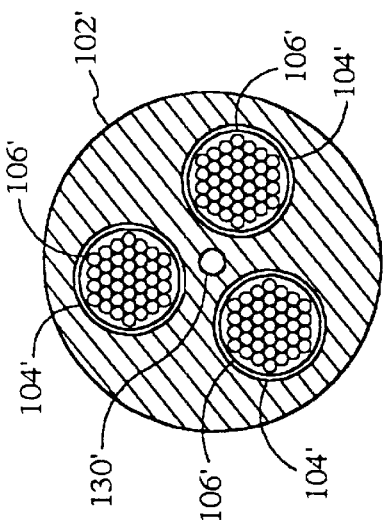
FIG. 2B is a representative detail view of the preferred embodiment shown in FIG. 2A taken along lines 2B—2B.

FIG. 2A is a representative perspective view of a preferred embodiment of a selective treatment of the endocardial/myocardial boundary system 100 of the present invention. FIG. 2B is a representative detail view of the preferred embodiment shown in FIG. 2A taken along lines 2B—2B. A main, outer tube 102 has at least one large lumen 104 extending therethrough. A plurality of mechanical or electromagnetic, such as optical fibers, or fiber bundles, or other functional devices 106 extend through the large lumen 104, from the proximal end 108 to the distal end 110. Appropriate blood seal means 112 will be known to those skilled in the art.

Figure 2D:
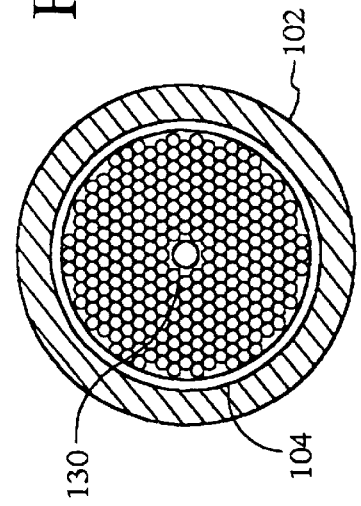
FIG. 2D is a representative detail view of the preferred embodiment shown in FIG. 2C taken along lines 2D—2D.

Additionally, a control tether 114 extends between the proximal end 108 of the apparatus, therethrough to the distal end 110 where it is coupled to a deflecting member 116. The tether 114 can run through the central lumen 104 in communication with the plurality of mechanical or electromagnetic functional devices 106 or the tether can be placed through an independent tether lumen 130 as shown in FIG. 2D. Either in construction or operation, as the plurality of mechanical or electromagnetic functional devices 106 are extended axially through the central lumen 104 and out the distal end 110 they are deflected from the axis in an outwardly splayed configuration. In the preferred embodiment shown, the deflecting member 116 can be controlled independently by manipulation of a handle portion 118 at the proximal end 120 of tether 114. Thus, the distal ends 122 of the plurality of mechanical or electromagnetic functional devices 106 can be controllably spaced into an operable and advantageous configuration to simultaneously or sequentially form a relatively dense pattern of pathways.

Figure 2C:
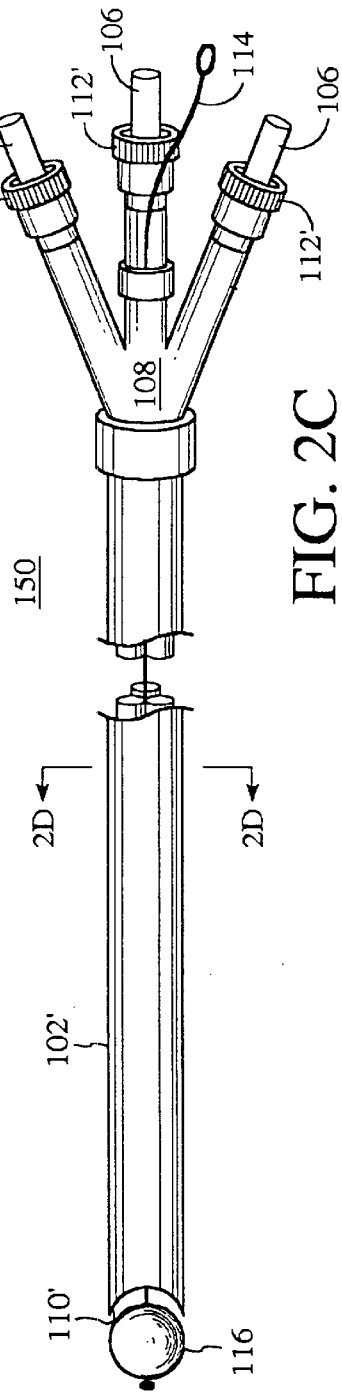
FIG. 2C is a representative perspective view of another preferred embodiment of a selective treatment of the endocardial/myocardial boundary system 150 of the present invention.

FIG. 2C is a representative perspective view of another preferred embodiment of a selective treatment of the endocardial/myocardial boundary system 150 of the present invention. FIG. 2D is a representative detail view of the preferred embodiment shown in FIG. 2C taken along lines 2D—2D. The central tube 102' can have any operable or advantageous number of elongated lumens 104' extending therethrough, and is preferably formed as an extrusion or molding. The trifurcated proximal end 108' has a plurality of blood seal means 112' and a plurality of mechanical or electromagnetic functional devices 106 enter the apparatus 150 therefrom. Tether 114 extends through an independent tether lumen 130' as well.

It will be understood that the plurality of mechanical or electromagnetic functional devices 106 can be any number of individual fibers, bundled or separated, and optical fiber devices which would be known to those skilled in the art would contain individual fibers with a range of diameters, such as anywhere between about 1000 microns to about 25 microns. As shown in FIGS. 2A and 2B, individual fibers can run commingled through the central lumen 104 and then be separated into two, three or more discrete fibers or bundles near the distal end 110 of the apparatus, and they can also be divided into separate bundles throughout the length of the apparatus 150. Furthermore, the portions of fibers extending past the distal end 110 or 110' and being deflected by deflecting member 116 can be wrapped clusters of fibers, individual fibers, etc. Fibers selected and sized at 100$\mu$ or less may be used to pierce to the desired depth for injury creation with or without sharpening or addition of a separate piercing mechanism.

FIGS. 3A–3E are representative perspective views of a preferred embodiment of the apparatus and method of selective treatment of the endocardial/myocardial boundary shown in FIGS. 2A and 2B. It will be understood that the system 100 shown can be introduced into the left ventricle 250 through a E10 separate guiding catheter or over a separate guide wire, etc., which are not shown. The apparatus can also be used or be adapted for use surgically or in minimally invasive surgical procedures.

Figure 3A:
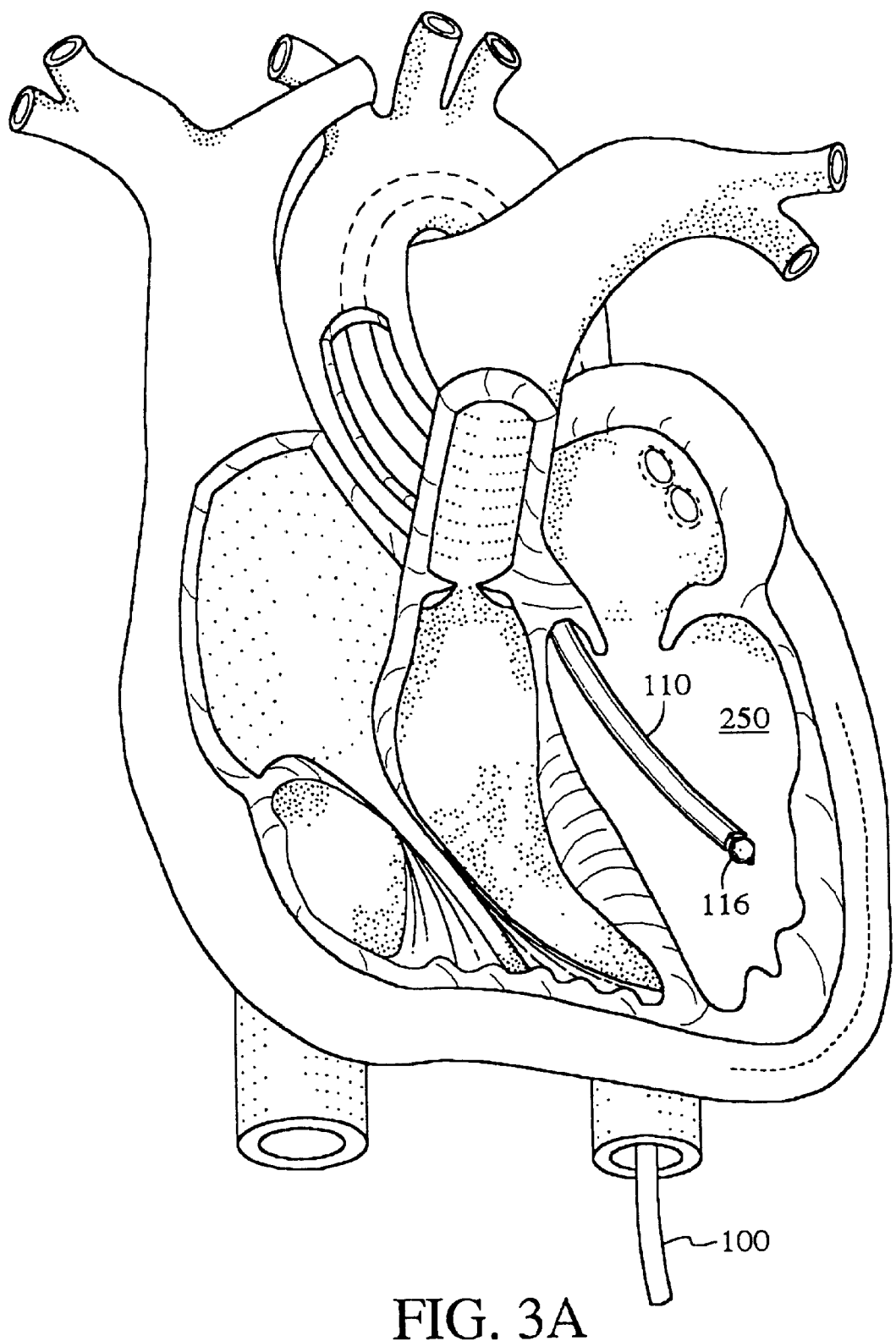
FIGS. 3A–3E are representative perspective views of a preferred embodiment of the apparatus and method of selective treatment of the endocardial/myocardial boundary shown in FIGS. 2A and 2B.
Figure 3B:
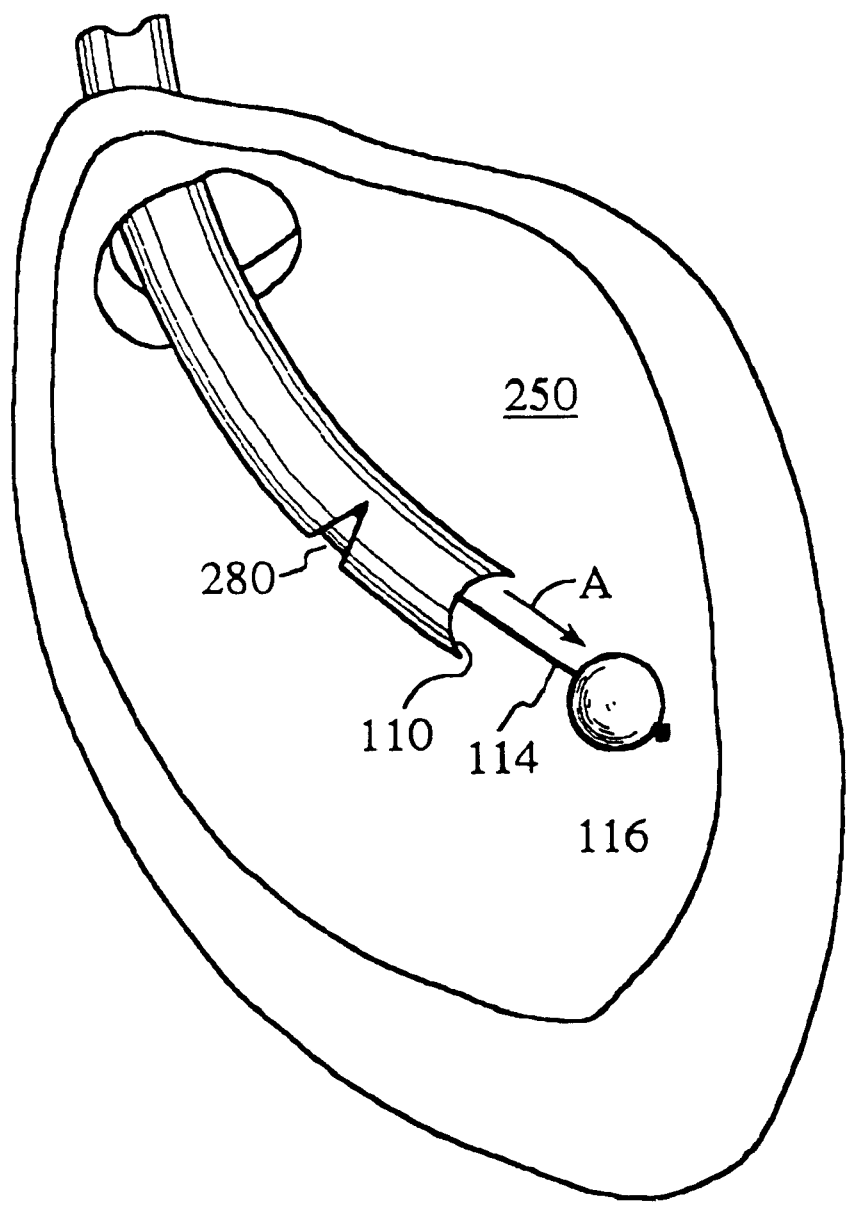
Figure 3C:
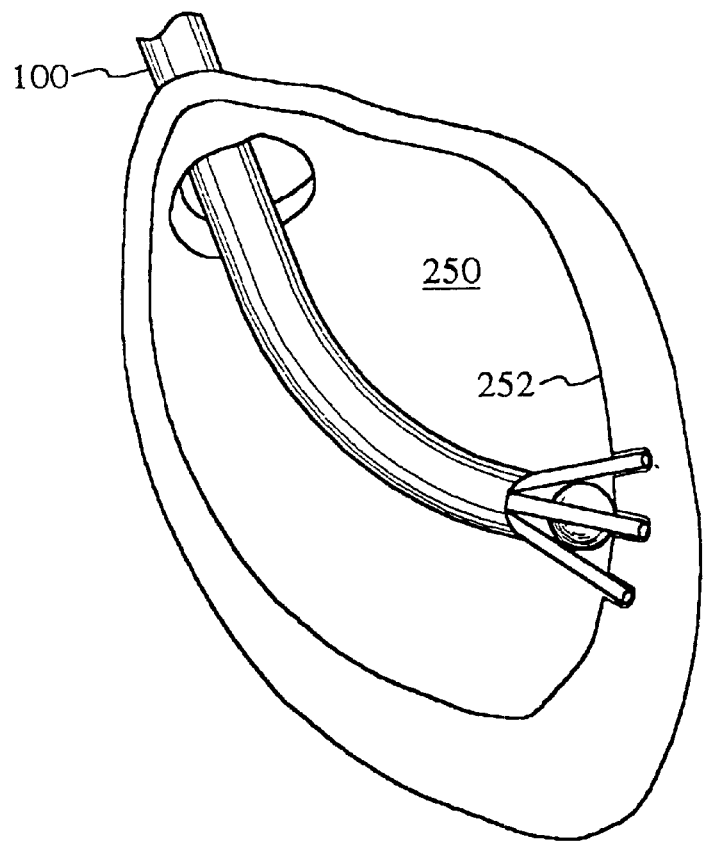

Introduced percutaneously into the left ventricle 250, the distal end 110 of the apparatus 100 can be positioned as desired as shown in FIG. 3A. Control of tether 114 will allow the operator or physician to advance the deflecting member 116 in the direction A as shown in FIG. 3B. As the plurality of mechanical or electromagnetic functional devices 106 pass through the distal end 110 of the apparatus 110, the distal ends 122 will be deflected away from each other, about deflecting member 116. It will be understood that once the deflecting member 116 is spaced as desired from the distal end 110 of the central tube 102, it can be placed directly on an endocardial surface 252 and the plurality of mechanical or electromagnetic functional devices 106 can be extended over the deflecting member 116 and into myocardium through endocardium. Alternatively, the plurality of mechanical or electromagnetic functional devices 106 can be extended over the deflecting member 116 and the entire distal end 110 of the apparatus can be extended so that the distal ends 122 pierce endocardium and penetrate myocardium, and the deflecting member 116 then comes to rest upon an endocardial surface 252. In the second instance, the deflecting member 116 acts as a depth stop, delimiting and otherwise preventing excessive or undesired advancement of the functional devices 106 into tissue.

Figure 3D:
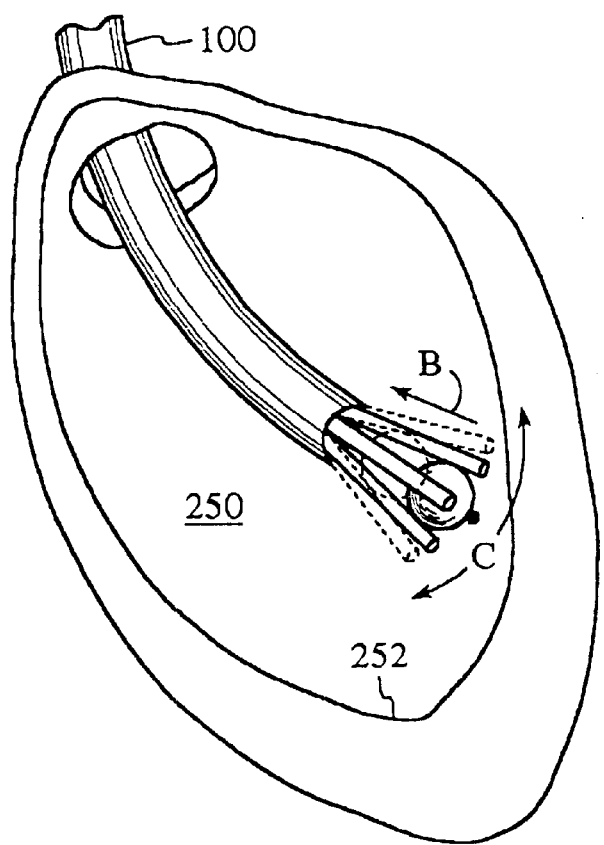

FIG. 3D shows retraction of the deflecting member 116, such as by control of tether 114, thereby causing movement of deflecting member 116 in a direction shown as B, and deflection of the distal ends 122 of the plurality of optical fibers, fiber bundles or other functional devices away from each other, or splayed out in direction C. Thus, as will be understood, further retraction of tether 114 relative to the functional devices 116 will cause continued or further splaying, deflection and separation of the distal ends 122 of the functional devices 116.

Figure 3E:
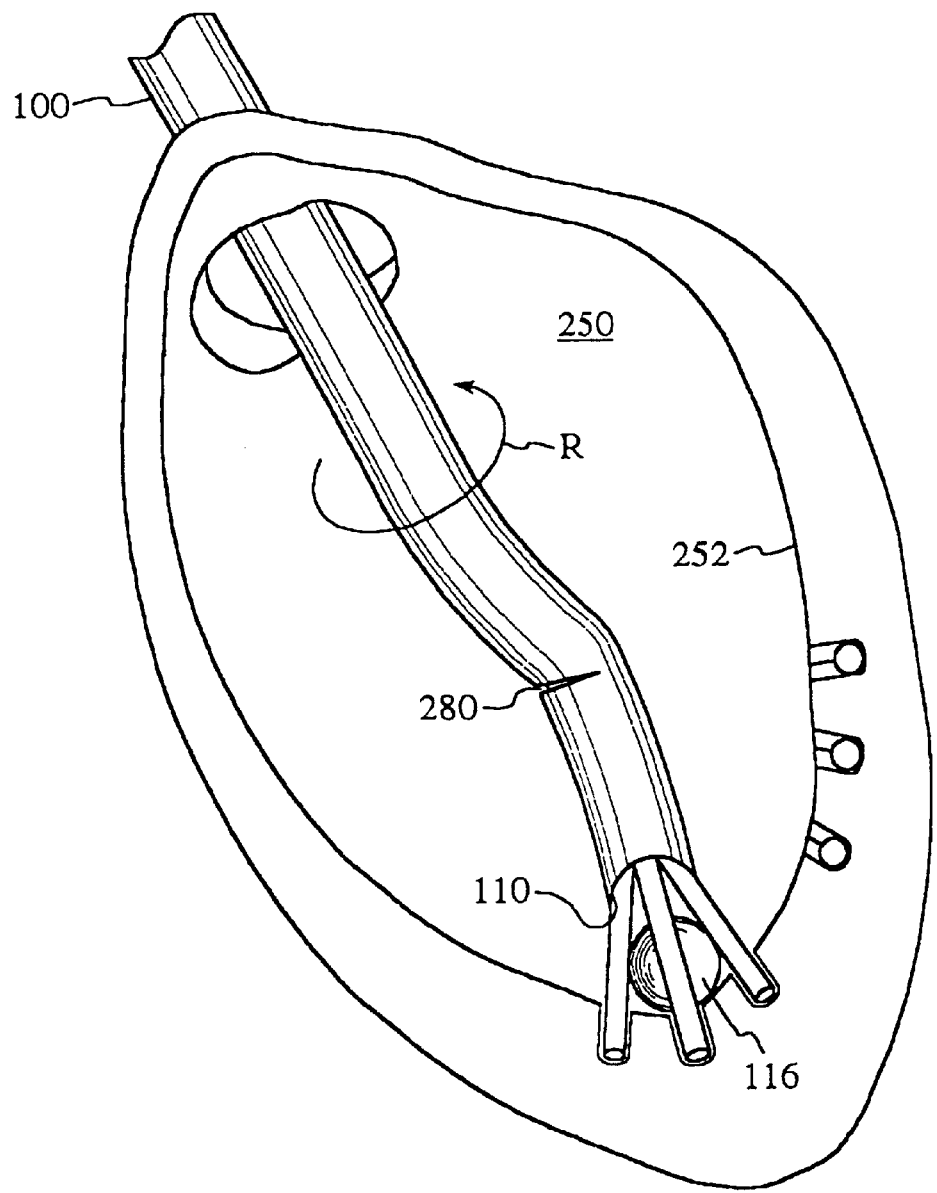

FIG. 3E shows a preferred embodiment of the apparatus 100 as shown in FIG. 2A in which the main outer tube 102 2has been angulated. Upon continued retraction of control tether 114 past the point at which the deflecting member 116 is at its maximum retraction, a secondary deflection occurs at notched portion 280 which collapses, thereby deflecting the distal end 110 of the apparatus 110 to a different portion of endocardial surface 252. Furthermore, rotation of apparatus 100, such as in direction R as shown, will position the distal end 110 into a plurality of different positions for extending endocardium. It will be understood by the foregoing that the notched portion 280 is optional and provides an additional degree of freedom for control. Substituting more traditional tensioning wire tip deflection systems, as commonly used in electrophysiology, would be an alternative and known apparatus for implementing "endocardial extension". The secondary angulation at one or more points along the outer tube 102 provides additional angulation control, specifically in catheter applications and surgical procedures involving an approach from lateral and posterior surfaces.

Figure 3F:
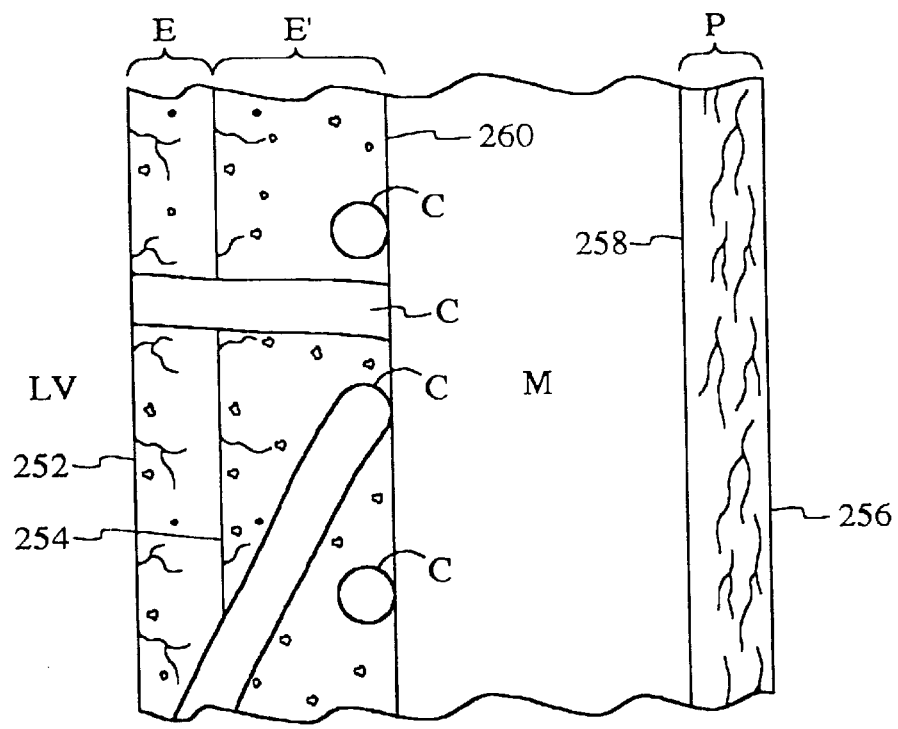
FIG. 3F is a representative section drawing of the treated area as formed by the apparatus and methods of the present invention.

FIG. 3F is a representative section drawing of the treated area El as formed by the apparatus and methods of the present invention. Adjacent the endocardial surface 252 there is the transitory zone 254 between endocardium E and myocardium M. On the opposite side of the tissue is the epicardial surface 256, epicardium P and the boundary 258 between the epicardium P and myocardium M. Upon formation of a plurality of injuries, piercing or zones of stimulation C, a new boundary 260 is formed in what was formerly conventional myocardium M and defining a new boundary E' between extended endocardium and conventional myocardium Thus, as shown diagrammatically, the original endocardium E becomes "extended" with communicating sinusoidal channels with enhanced blood wash and flow into the extended endocardium area E' thereby enhancing blood flow deeper into the myocardium by forming greater surface area of exchange at new boundary 260. It will be noted that performing the described "endocardial extension" is important and valuable because it supplements supply from the coronary arteries which generally supply most of the myocardium with oxygenated blood. In almost all cases of coronary disease, however, this function of the coronary arteries is essentially impaired.

Figures 4A, 4B:
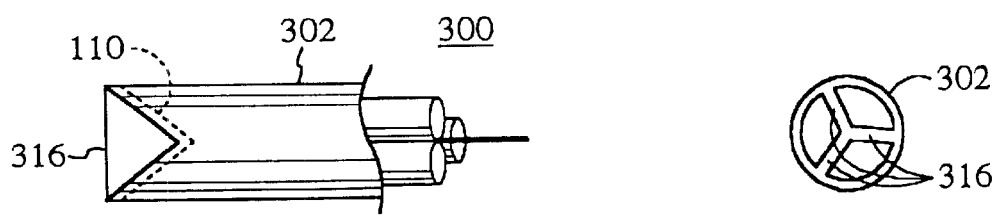
FIGS. 4A and 4B are representative isometric and section views, respectively, of a preferred embodiment of a selective treatment of the endocardial/myocardial boundary system 300 of the present invention.

FIGS. 4A and 4B are representative isometric and section views, respectively, of a preferred embodiment of a selective treatment of the endocardial/myocardial boundary system 300 of the present invention. In this embodiment, the deflecting member 316 is integral and internal to the distal end 110 of central tube 302. The deflecting member 316 can be a section located at the distal end 110 only, or the central tube 302 can be formed as an extrusion with three or more or less distinct and separate channels running through the tube 302 and effectively deflecting or splaying the distal ends of the functional devices 106 away from each other.

Figure 4C:
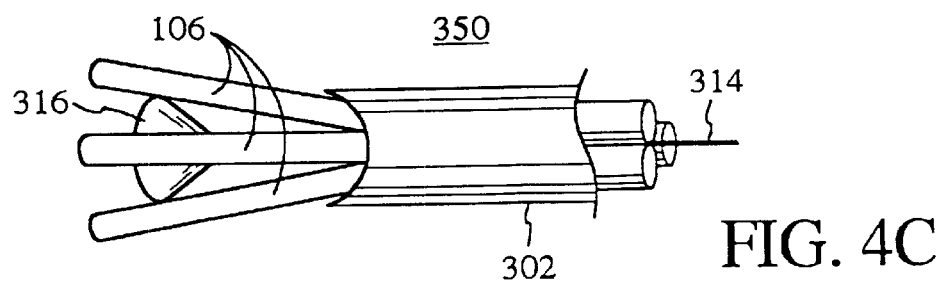
FIG. 4C is a representative view of another preferred embodiment of a selective treatment of the endocardial/myocardial boundary system 350 of the present invention.

FIG. 4C is a representative view of another preferred embodiment of a selective treatment of the endocardial/myocardial boundary system 350 of the present invention. In this embodiment, the deflecting member 316 is cone shaped. Upon extension of mechanical or electromagnetic functional devices 106 through the central tube 302, the distal tips 122 are deflected or splayed away from each other, creating a tool sufficient for forming a plurality of laser or mechanically created injuries, pierce or stimulation zones in endocardial tissue. It will be understood that the precise shape of deflecting member 316 can be varied, but will preferably cause little undesired friction between the distal ends 122 of the mechanical or electromagnetic functional devices 106 and the deflecting member 316. Additionally, control tether 314 can be fixed or permanent, thus providing optional independent control of deflecting member 316.

It will be understood from the foregoing, therefore, that the deflecting member can have a plurality of different sizes, shapes and configurations. To expand and clarify, the deflecting member 116 portion can be movable or retractable, such as mounted on a tether 114 as shown in FIGS. 2A, 2C, 3A–3E, etc. The deflecting member 116 can also be fixed in place with regard to the outer tube 102, and can comprise a discrete number of deflecting ramps, grooves, slots, or guide channels. Additionally, the deflecting member 116 can be located well within the distal end of the outer tube 102, just inside or outside of the distal end 110 of the outer tube, or it can be located a short distance beyond the distal end 110 of the outer tube 102.

Figure 5A:
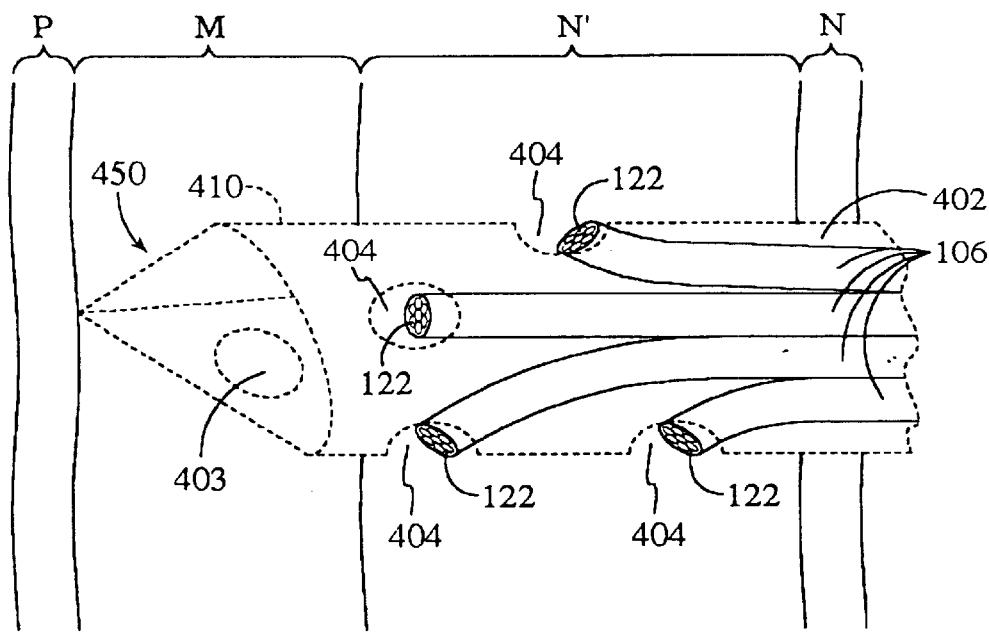
FIG. 5A is a representative section view of a preferred embodiment of a selective treatment of the endocardial/myocardial boundary system 400 of the present invention.
Figure 5B:
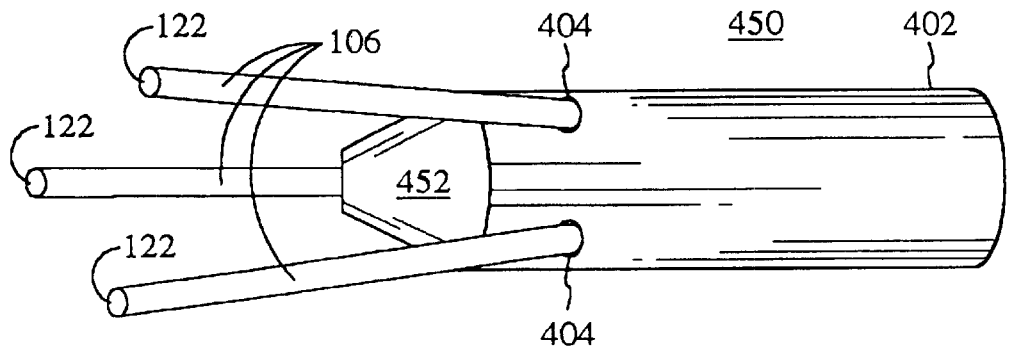
FIG. 5B is a representative section view of another preferred embodiment of a selective treatment of the endocardial/myocardial boundary system 450 of the present invention.

FIG. 5A is a representative section view of a preferred embodiment of a selective treatment of the endocardial/myocardial boundary system 400 of the present invention. FIG. 5B is a representative section view of another preferred embodiment of a selective treatment of the endocardial/myocardial boundary system 450 of the present invention. In each of these embodiments, the mechanical or electromagnetic functional devices 106 are disposed either fixedly or movably, such as by advance or retraction, within hollow lumens within the central tube 402.

In the embodiment shown in FIG. 5A, the distal ends 122 of the mechanical or electromagnetic functional devices 106 are disposed immediately adjacent small apertures 404 within the distal end 410 of central tube 402. The individual mechanical or electromagnetic functional devices 106, such as fiber bundles, can be positioned permanently within the central tube 402 such that laser energy or other type of energy from the distal tips 122 can reach target tissue, but the distal tips 122 won't cause unintended or undesired trauma or injury to tissue which the apparatus 401 is being advanced into.

A pointed piercing tip 450 can be inserted through endocardium N and into myocardium M. New treatment area N' is formed as shown. The piercing tip 450 can have any conventional or custom shape or design characteristic, including sharpened to a point, blade end, cross-cut, centerradiating multi-blade castings or extrusions, hollow piercing needle, etc. An optional sensor, such as a conventional pressure transducer 403, may be placed at the tip 450 to determine peak pressure if use of the treatment device is to be correlated with wall thickness. For instance, laser energy or piercing may occur at maximum pressure to ensure maximum tissue penetration in certain boundary areas. Signals from the pressure transducer may be used to enable the laser, and absence of a maximum signal prevents laser firing.

As shown in FIG. 5B, the apparatus 450 has a blunt tip 452. The mechanical or electromagnetic functional devices 106, such as individual fibers, are shown advanced through individual windows 404 at the distal end 410 of central tube 402. In both embodiments, as mentioned above, the internal lumen or lumens of the central tube 402 encase the mechanical or electromagnetic functional devices 106. In a single lumen hollow tube with a plurality of small apertures 404, the fibers would all be bundled together. Alternatively, the central tube may have a plurality of different, even differently shaped or organized, hollow internal lumens such as formed by extrusions, moldings, etc., which would provide a plurality of lumens for independently operable mechanical or electromagnetic functional devices 106.

Extension and/or retraction of the distal ends 122 of the mechanical or electromagnetic functional devices 106 could be before or after bearing the distal blunt, stabilizing end 452 against an endocardial surface, and it will be understood that the mechanical or electromagnetic functional devices 106 could be extended or retracted one at a time, or simultaneously.

The apparatus shown in FIG. 5B is especially suitable for surgical, and especially minimally invasive surgical use. Tissue can be pierced to a desired, calculated or otherwise determined depth and then mechanical or electromagnetic energy devices can then be extended through the pierced opening.

FIGS. 6A and 6B are representative cross sectional and section views, respectively, of another preferred embodiment of a selective treatment of the endocardial/myocardial boundary system 500 of the present invention. As an alternative embodiment of the invention to the single strand or bundle version previously described, a selective treatment of the endocardial/myocardial boundary system 500 may be provided which has a plurality of spaced apart treatment devices. A selective treatment of the endocardial/myocardial boundary system 500 has, for example but not limited to, four relatively smaller optical fiber strands 502 which project outwardly like an axially parallel, spaced apart group of prongs from a transverse stop member 504 at the distal end of the selective treatment of the endocardial/myocardial boundary system 500. Each of these smaller fiber strands 502 has a diameter of around 0.1 to 0.5 mm and its distal tip 506 may be blunt or beveled. The length of these optical prong-like strands is roughly the estimated thickness of the endocardium, e.g. 1.5 to 3.0 mm and despite their relatively small diameter these prong-like elements are quite rigid. Inwardly from the stop member 504 the smaller fiber strands 502 are preferably held together by suitable potting compound 508 which is surrounded by a plastic sheath 510.

During a selective treatment of the endocardial/myocardial boundary procedure using the treatment system 500, the apparatus is pushed against the wall of the heart until the distal tips 506 of the spaced apart projecting strands 502 penetrate into myocardium. Alternatively, laser energy may be used to penetrate the wall. As with previous embodiments, laser power is triggered to emit laser energy from the distal tips of the strands after they are moved forward in increments to form channels or stimulus pockets beyond each distal tip within the myocardium tissue. As laser energy is emitted from the distal end of each fiber strand 502, following each interval of penetration, a network or matrix of interconnected, sinusoidal passages, channels or stimulus pockets is created within the myocardium. In this embodiment, as well as in embodiments showing multiple treatment devices, treatment produces interstial areas of untreated tissue surrounding by treated areas thereby promoting angiogenesis.

As another approach to selective treatment of the endocardial/myocardial boundary, retro-lasing can be performed. This novel method includes the steps of advancing the distal tip or tips of laser delivery means such as mechanical or electromagnetic functional devices a selected distance into the myocardium and then delivering laser energy to create a selective treatment of the endocardial/myocardial boundary channel or other treatment site while simultaneously retracting the fiber, laser delivery means or other functional device. With this procedure, inasmuch as laser energy is only delivered during retraction of the fiber, the possibility of advancing the fiber too far and lasing through an epicardial surface is reduced, and the risks of complications arising from such epicardial perforations, including but not limited to cardiac tamponade (a buildup of pressure in the pericardial sac caused by the presence of an excess of fluid such as blood), proliferation of adhesions between the epicardium and the pericardial sac (thereby preventing normal, frictionless enclosure of the heart muscle within the pericardial sac), etc., are minimized.

Furthermore, adjunct use of appropriate drug delivery apparatus, blood seal means, depth stop apparatus, visualization means, marker means as well as other hardware and methodology will be considered within the scope of the present invention. Additionally, use of electrophysiology (EP) readings and readings from other sensors positioned at the distal tip 118 for confirming tissue contact, such as with an electrode along with or instead of the pressure transducer 403 FIG. 5A, temperature, conductivity, density, durometer, porosity, permeability or other mechanical, chemical or electrical characteristic of tissue will be particularly useful.

The present invention is intended for use with any medical laser. In particular, the Holmium or excimer laser is particularly suited to the present invention. However, any suitable laser source, pulsed or otherwise, could provide laser energy to the laser delivery means of the present invention for performing the method of the present invention. Likewise, the catheter and surgical equipment, including laser delivery means, referred to in the present document as well as that known and used in medicine and other disciplines today and in the future, will be included in the scope of this disclosure. Such laser delivery means include, but are not limited to, individual optical fibers as well as bundles of fibers with and without piercing tips and with or without firing tips or fiber ends having shaped or contoured end faces for selectively diverging the laser beam or other laser energy diverging means, rods, mirrors configurations and other laser delivery means with and without focusing lens and the like. It will also be understood that the apparatus and method of the present invention as described herein including the novel combination or use with of any conventional mechanism or method which are known to those skilled in the art, are included within the scope of this invention. Furthermore, with regard to non-laser selective treatment of the endocardial/myocardial boundary, a cannula or trocar assembly may be extended into the tissue of the left ventricle, with or without use of a mechanical piercing tool.

It will further be understood that while the present invention has been described for selective treatment of the endocardial/myocardial boundary from endocardial surfaces in the left ventricle, the apparatus and methods described herein are equally intended for use in any suitable procedure, including but not limited to procedures where any device need be extended through a guide catheter to an opening or other point within the body for other medical procedures including laser treatment, visualization, biopsy, etc. "Stimulation", for example, is performed by using laser energy to create zones or pockets, optionally interconnected at least initially by small channels ablated through the tissue, for the introduction of blood born growth and healing factors and stimulated capillary growth surrounding the lased zones or pockets to create an increased supply of oxygen to the tissue and thus a revitalization of the heart muscle. Methods and apparatus for causing stimulation are more fully described in co-pending U.S. patent application Ser. No. 08/664,956 filed Jun. 13, 1996 entitled INTRAOPERATIVE MYOCARDIAL DEVICE AND STIMULATION PROCEDURE.

Figure 7A:
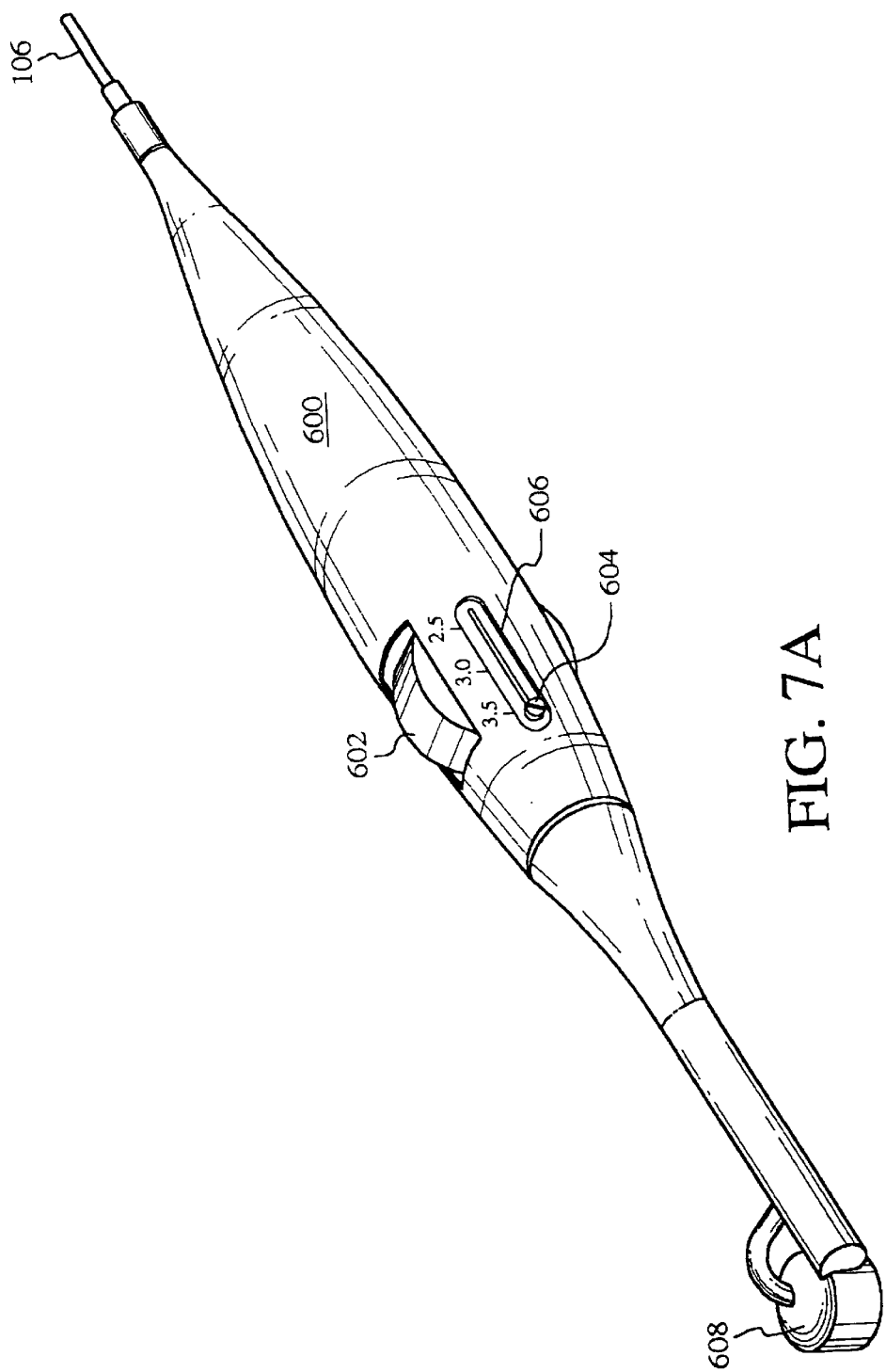
FIG. 7A is an isometric view of an apparatus for forming branched, contiguous, multi-channeled, sinusoidal and interconnected treatment zones for selective treatment of endocardial/myocardial boundary.

FIG. 7A is an isometric view of an apparatus 600 for forming branched, contiguous, multi channeled, sinusoidal and interconnected treatment zones for selective treatment of endocardial/myocardial boundary. FIG. 7B is a representative view of a branched, contiguous, multichanneled, sinusoidal and interconnected treatment zone. The apparatus is more fully described in U.S. Pat. No. 5,766,698 filed Jul. 3, 1996 entitled CONTIGUOUS, BRANCHED TRANSMYOCARDIAL REVASCULARIZATION (TMR) CHANNEL, METHOD AND DEVICE issued Jun. 16, 1998. Thumb wheel 602 is used to advance a mechanical or electromagnetic energy functional device 106 through the handpiece and out the rotating head section 608. The distance which the fiber is advanced is controlled by a laser delivery means slider depth adjust means 604. The maximum depth of the injury which is to be created by the handpiece can be set precisely and conveniently by locating the side slider at the appropriate axial position, as indicated by a scale or other reference means 606.

Thus, contiguous, branched injuries 650 which originate at a single point 652 in either endocardium or epicardium 654 develop along a plurality of radiating, ultimately independent paths, through at least portions of myocardium 656 and into endocardium, to permit capillary communication and enhanced myocardial infusion of oxygenated blood, growth, healing, and other factors. Such apparatus is particularly suitable for surgical procedures, such as in open heart or minimally invasive surgery (MIS).

Figure 8:
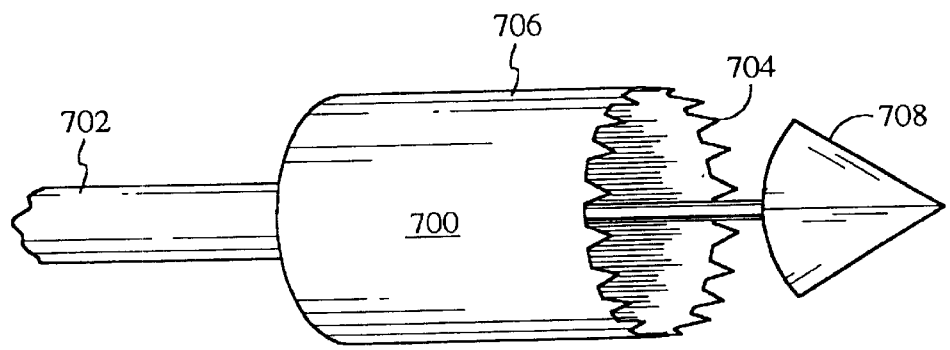
FIG. 8 is a representative section view of rotating mechanical drill type apparatus 700 for forming sinusoidal and interconnected channels or treatment zones in endocardial/myocardial boundary.

FIG. 8 is a representative section view of rotating mechanical drill type apparatus 700 for forming sinusoidal and interconnected treatment zones in the endocardial/myocardial boundary. The apparatus 700 has a mounting shaft 702 and a set of cutting teeth 704 spaced around the perimeter of circular spinning sleeve 706. Optionally, an advancable or extendable pointed piercing cone or pyramid shaped tip 708 can be used in conjunction with the spinning cutting device to pierce tissue to act as an introducer and the piercing tip 708 will part off, penetrate and/or pierce the tissue' easily.

Figure 9:
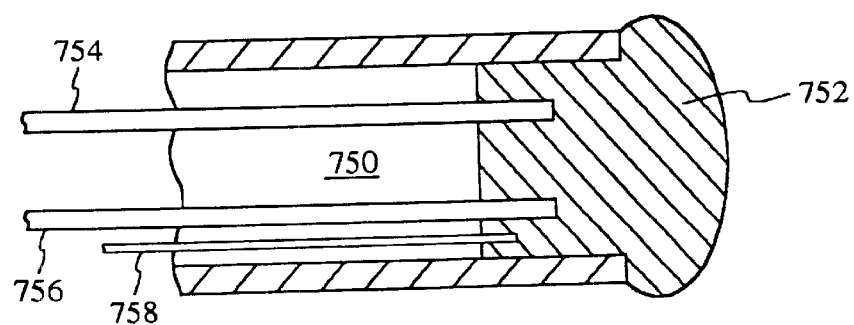
FIG. 9 is a representative section view of resistance type heating tip apparatus 750 for forming sinusoidal and interconnected channels or treatment zones in endocardial/myocardial boundary.

FIG. 9 is a representative section view of resistance type heating tip apparatus 750 for forming treatment zones in endocardial/myocardial boundary. A distal tip 752 is resistively or inductively heated by conductors 754 and 756. The operating temperature of the distal tip 752 is sufficient to form channels or cause stimulation of myocardial tissue. A thermocouple or other temperature sensing device 758 may be imbedded into the distal tip 752 to determine the temperature thereof. The signal developed by the sensing device 758 may be used to control the electrical power to the distal tip 752 in a conventional manner.

Figure 10:
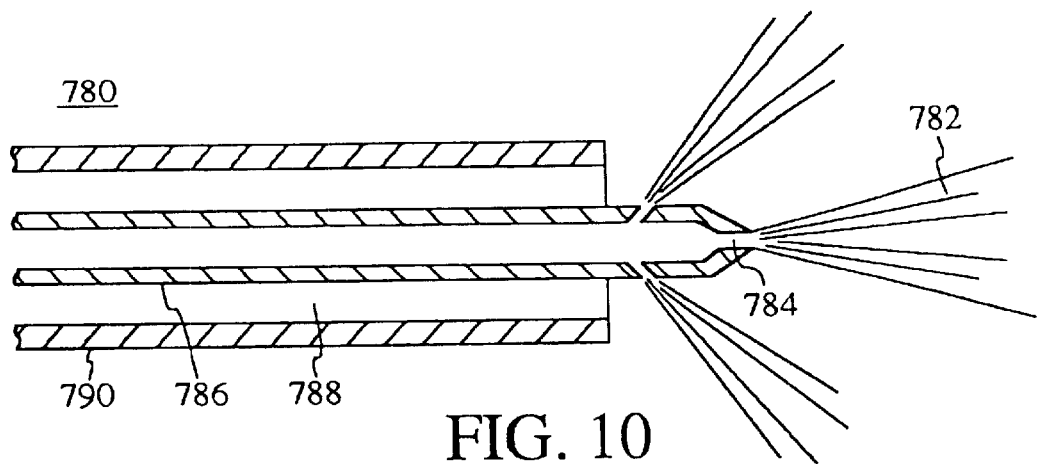
FIG. 10 is a representative section view of fluid jet nozzle apparatus 780 for forming sinusoidal and interconnected channels or treatment zones in endocardial/myocardial boundary.

FIG. 10 is a representative section view of fluid jet nozzle apparatus 780 for forming sinusoidal and interconnected injury or treatment zones in endocardial/myocardial boundary. One or more high velocity fluid jets 782 are emitted from a discharge tip 784 in the distal end of inner tubular member 786 is used to form the channel or stimulation zone. Debris from the channel forming operation is aspirated away from the site through annular lumen 788 formed between the inner tubular member 786 and outer tubular member 790. By directing jets of pressurized fluids at selected positions within myocardium, tissue can be mechanically disrupted and thereby removed.

Figure 11:
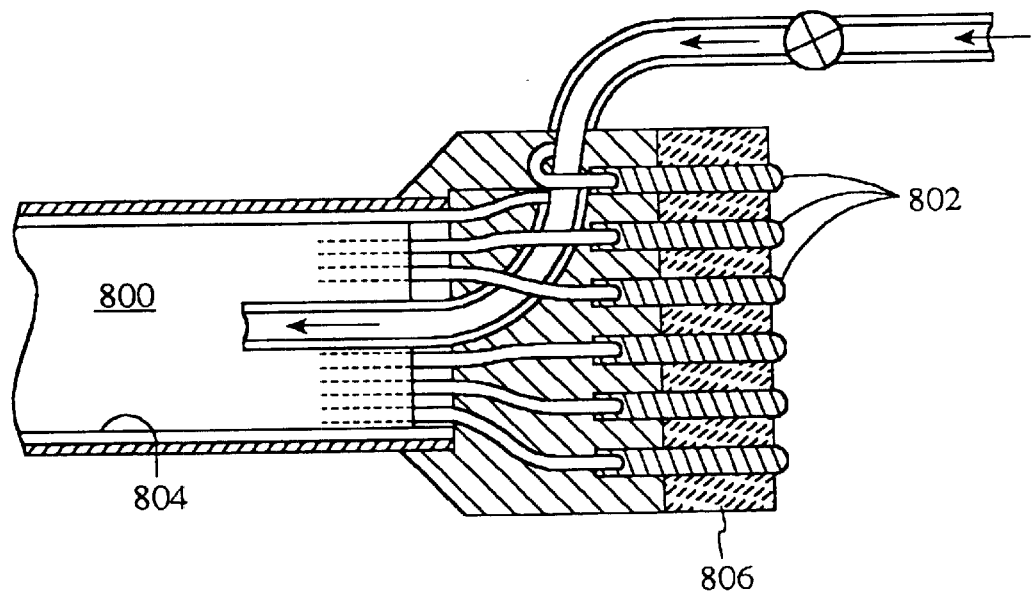
FIG. 11 is a representative section view of radio frequency apparatus 800 for forming sinusoidal and interconnected channels or treatment zones in endocardial/myocardial boundary.

FIG. 11 is a representative section view of radio frequency apparatus 800 for forming sinusoidal and interconnected injury or treatment zones in endocardial/myocardial boundary. A method of use includes positioning an array of active electrodes 802 in close proximity to a target site on the wall of a patient's heart, and applying a high energy, operative frequency, such as a radio frequency, between the active electrodes 802 and a return electrode 804 to ablate tissue at the heart wall. The high frequency energy ablates, i.e. volumetrically removes the heart tissue, and the electrodes 802 and the distal tip 806 of the apparatus 800, when the energy supplied is properly controlled, will bore a plurality of channels, pathways or interconnections through the heart tissue. Such radio frequency apparatus are more fully described in International Publication Number WO 97/18768 published May 29, 1997 entitled SYSTEMS AND METHODS FOR ELECTROSURGICAL MYOCARDIAL REVASCULARIZATION.

Figure 12C:
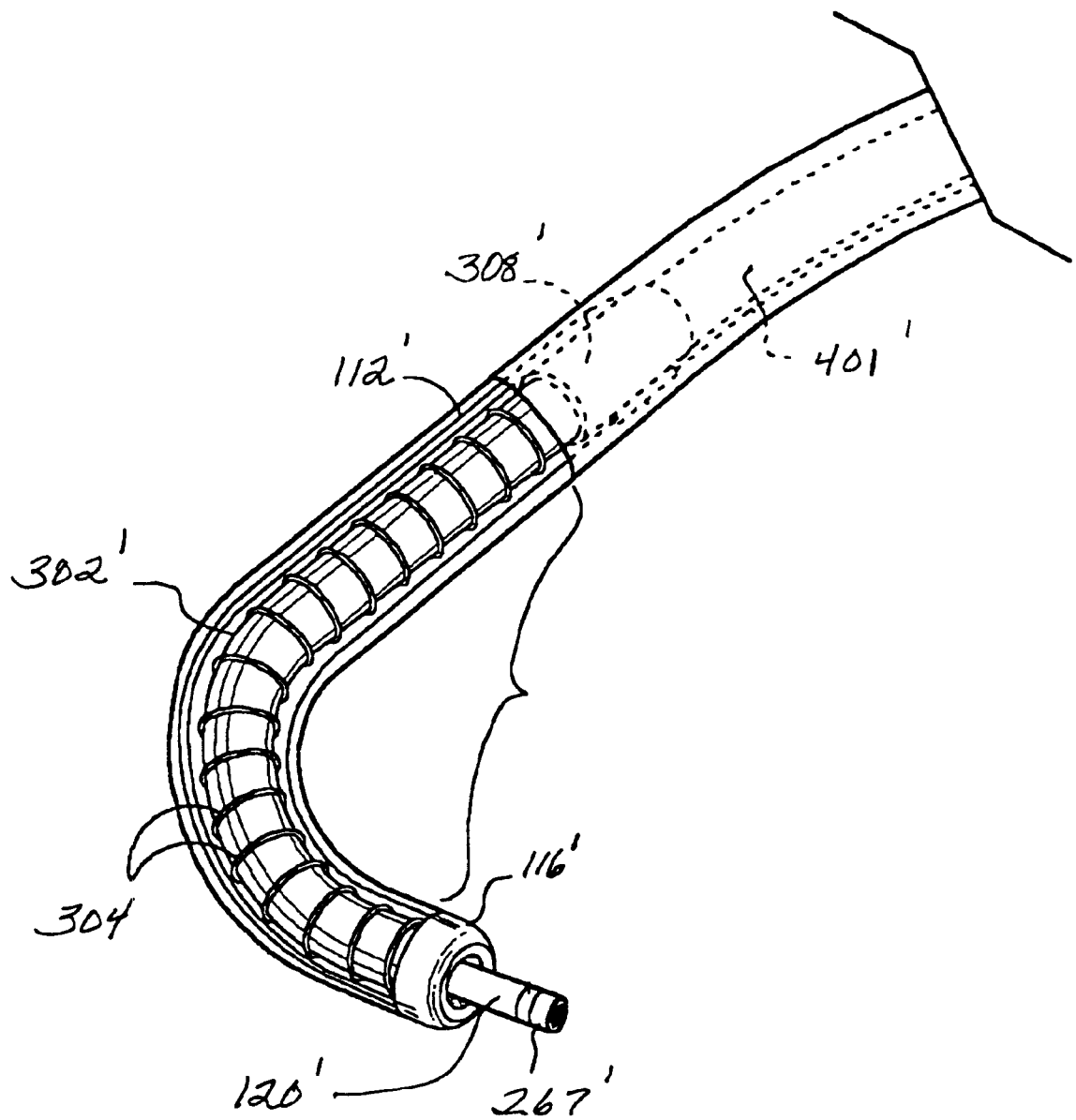

FIGS. 12A, 12B and 12C are representative isometric and section views of the distal end and steering system of a preferred embodiment of a catheter ultrasound guidance system 300' for forming treatment zones in endocardial/myocardial boundary. A matching layer 110', gold trace 106', transducer crystal 104', backing 114', coaxial cable 112' and housing 116' are assembled together. Mounting face 130' couples to the distal tip 303' of catheter 300'. It will be understood by those known in the art that such coupling means includes, and is not limited to, bayonet and other quick connect mounts, screw on or press fit/snap on couplings, etc.

The catheter 300' is steerable and has steering means as described herein. A central catheter tube 302' terminates in the distal tip 303'. A spiral spring member 304' made of a radiopaque material adds visibility to the bend radius of the apparatus and enhances steerability of the apparatus 300'. A flat planar, rigid shim 306' couples between the distal tip 303' of the catheter 300' and an intermediate sleeve 308'. A pull cable 310' also attaches to the distal tip 303' opposite the annular opening 312' through the distal tip 303' so as to act upon the distal tip 303' and cause deflection of the shim 306' as desired to steer the distal tip 303' to selected regions or surfaces. An outer jacket 314' protects the catheter assembly 300'. Embodiments of the steerable catheter apparatus with the ultrasound guidance system are described in U.S. patent application Ser. No. 08/852,977 filed May 7, 1997 entitled ULTRASOUND DEVICE FOR AXIAL RANGING and incorporated herein in its entirety. Embodiments of the steerable catheter apparatus of the present invention without the ultrasound guidance system are described in U.S. patent application Ser. No. 08/833,352 filed Apr. 4, 1997 entitled STEERABLE CATHETER and incorporated herein in its entirety. The device preferably is approximately 7 French and uses a fiber bundle 0.5 mm or less in diameter for endocardial extension.

Additionally, the ultrasound device may be used with curved or pre-bent catheters for delivery of a single optical fiber with or without a lens device for operatively, selectively and/or controllably directing laser energy. Such devices can be easily manipulated to create dense injury patterns and ultrasound ranging can be used to control the depth and select depth. Additionally, piercing, analysis or other procedure can be carried out at an angle, thereby providing enhanced depth control.

The catheters of the present invention are especially suitable for medical procedures, including TMR, when operated in conjunction with optical fiber laser delivery means. Such optical fibers or fiber bundles utilize individual fibers from 25 to 1000 microns, or more or less. By way of example only, and not limited to the following, typical catheters of the present invention may have a diameter equivalent to between about 5 and about 7 French in which fibers or fiber bundles between about 250 and about 500 microns are used for laser energy delivery.

Laser firing can be controlled by any known or other specific means. Such control means include laser interlock with contact electrodes, distally mounted pressure transducer, etc. Pace control, or control of the laser as a function of the heart beat, can be implemented, including synchronous, asynchronous, or random pathway creation relative to the heart beat. Additionally, operator signals such as lights, audible signals, etc. may be used to facilitate and/or coordinate operation by the cardiology operating room team. Suitable sensors may be mounted on the distal-most tips or front faces of the devices, such as (but not limited to) those shown in FIGS. 2, 4, 5, 6, 9 and 11.

Furthermore, smaller, more singular, generally lower power settings differentiate or characterize systems used for laser assisted endocardial extension methods of the present invention from that of typical TMR or PTMR procedures. By way of example, but not limited to in any way, typical power settings for a holmium laser might be 3.5 watts for a single pulse injury where such a single pulse injury is repeated multiple times to form a dense pattern of injuries greater than 1 mm apart.

It will be understood by the foregoing discussion that numerous means for creating the channels or zones of stimulation will be known to those skilled in the art, and are included within the scope of this application. Mechanical means, include piercing, cutting, flushing, reaming, ultrasound and other devices and methods. Such will also include any adjunct structural enhancements, such as for visualization. Electromagnetic energy will also include radio frequency, laser energy, thermal energy, etc. Such means will be referred to hereafter, generally, as mechanical and thermoelectric energy functional devices.

Unless defined otherwise, all technical and scientific terms used herein have the same meaning as commonly understood by one of ordinary skill in the art to which this invention belongs. Although any methods and materials similar or equivalent to those described can be used in the practice or testing of the present invention, the preferred methods and materials are now described. All publications and patent documents referenced in this application are incorporated herein by reference.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true purview, spirit and scope of the invention.

What is claimed is:

1. A method of treating boundary areas in myocardium within the left ventricle of the heart including the following steps:

provinding an apparatus having proximal and distal ends, at least one lumen therein, a steering mechanism operable from the proximal end and extending to the distal end, at least one treatment device having a treatment diameter substantially no greater than 1.0 mm slidably extendable through the at least one lumen and through the distal end wherein one of said at least one treatment device is a mechanical device having a first piercing tool, and a second piercing tool having a piercing diameter substantially no greater than 1.0 mm for creating a pilot entry path for the at least one treatment device to reach a selected boundary area;

placing the distal end of such apparatus on a surface of the heart;

advancing the second piercing tool through the surface a distance selected to reach the boundary area;

advancing the at least one treatment device through a pilot entry created by the second piercing tool until a distal end thereof reaches the boundary area; and operating the at least one treatment device having the mechanical device with the first piercing tool to create a pattern of injury sites at the boundary area, the pattern having injuries no greater than 3.0 mm in diameter with each injury in the pattern spaced approximately no more than 1 cm from each contiguous injury.

2. The method of claim 1 wherein a second of said at least one treatment device is a laser device and the step of creating the pattern of injury sites is performed using laser energy from the laser device.

3. The method of claim 2 further comprising operating the laser at a power level of 3.5 watts and creating each injury with a single pulse of energy delivered through a fiber element having a diameter of 1 mm.

4. The method of claim 3 further comprising the step of delivering holmium laser energy through the fiber element to create each injury.

5. The method of claim 2 further comprising providing an excimer laser to deliver laser energy through the fiber element.

6. The method of claim 1 wherein the step of advancing the second piercing tool further comprises advancing the second piercing tool through endocardium to reach myocardium bordering the endocardium, and the step of operating the at least one treatment device to create a pattern of injury sites further comprises creating sufficient injury sites to create a sinusoidal, spongy mesh of interconnecting passageways in the bordering myocardium for enhancing blood flow through the endocardium into the myocardium bordering the treated myocardium.

7. The method of claim 1 further comprising providing a radio frequency treatment device.

8. A method of treating boundary areas in myocardium within the left ventricle of the heart including the following steps:

providing an apparatus having proximal and distal ends, at least on lumen therein, a steering mechanism operable from the proximal end and extending to the distal end, at least two treatment devices having a treatment diameter substantially no greater than 1.0 mm slidably extendable through the at least one lumen and through the distal end, and a piercing tool having a piercing diameter substantially no greater than 1.0 mm for creating a pilot entry path for the at least one treatment device to reach a selected boundary area;

placing the distal end of such apparatus on a surface of the heart;

advancing the piercing tool through the surface a distance selected to reach the boundary area;

advancing the at least one treatment device through a pilot entry created by the piercing tool until a distal end thereof reaches the boundary area; and operating the at least two treatment devices simultaneously to create a pattern of injury sites at the boundary area, the pattern having injuries no greater than 3.0 mm in diameter with each injury in the pattern spaced approximately no more than 1 cm from each contiguous injury.

9. The method of claim 8 further comprising the step of spreading distal tips of the at least two treatment devices apart to form treatment ends deflected approximately 1 to 45 degrees relative to a central axis of the apparatus.

10. A method of treating boundary areas in myocardium within the left ventricle of the heart including the following steps:

providing an apparatus having proximal and distal ends, at least on lumen therein, a steering mechanism operable from the proximal end and extending to the distal end, at least one treatment device having a treatment diameter substantially no greater than 1.0 mm slidably extendable through the at least one lumen and through the distal end, a pressure transducer at the distal end, and a piercing tool having a piercing diameter substantially no greater than 1.0 mm for creating a pilot entry path for the at least one treatment device to reach a selected boundary area;

placing the distal end of such apparatus on a surface of the heart;

advancing the piercing tool through the surface a distance selected to reach the boundary area;

advancing the at least one treatment device through a pilot entry created by the piercing tool until a distal end thereof reaches the boundary area;

operating the treatment device to create a pattern of injury sites at the boundary area, the pattern having injuries no greater than 3.0 mm in diameter with each injury in the pattern spaced approximately no more than 1 cm from each contiguous injury; and monitoring pressure at the myocardium with said pressure transducer to control timing of treatment.

\* \* \* \* \*